United States Patent [19]
Lin et al.

[11] Patent Number: 6,133,496
[45] Date of Patent: Oct. 17, 2000

[54] TWO-STAGE ISOMERIZATION OF SATURATED C6 HYDROCARBONS

[75] Inventors: Fan-nan Lin, Bartlesville, Okla.; Edgar Durand Davis, Borger, Tex.

[73] Assignee: Phillips Petroleum Company, Bartlesville, Okla.

[21] Appl. No.: 09/265,071

[22] Filed: Mar. 9, 1999

[51] Int. Cl.⁷ .................................................. C07C 5/22
[52] U.S. Cl. .................... 585/736; 585/734; 585/738; 585/748
[58] Field of Search .................... 585/734, 736, 585/738, 748, 310, 317; 208/63, 65

[56] References Cited

U.S. PATENT DOCUMENTS

| | | | |
|---|---|---|---|
| 2,505,792 | 5/1950 | Ross et al. ............................ | 260/666 |
| 2,915,571 | 12/1959 | Haensel .............................. | 260/683.68 |
| 2,972,650 | 2/1961 | Burk et al. ............................ | 585/736 |
| 3,007,985 | 7/1961 | Binning .............................. | 585/736 |
| 3,054,832 | 9/1962 | Cabbage ............................. | 260/666 |
| 3,233,001 | 2/1966 | Merryfield et al. ................. | 260/666 |
| 3,277,194 | 10/1966 | Cabbage ............................. | 260/666 |
| 3,631,117 | 12/1971 | Kovach et al. ..................... | 260/666 |
| 3,974,061 | 8/1976 | Quisenberry ....................... | 208/65 |
| 4,149,993 | 4/1979 | Rao et al. ............................ | 252/442 |
| 4,655,484 | 4/1987 | Rahlwes ............................. | 585/253 |
| 4,783,575 | 11/1988 | Schmidt et al. .................... | 585/748 |
| 5,059,741 | 10/1991 | Foley ................................ | 585/734 |
| 5,326,925 | 7/1994 | Sachtler ............................. | 585/736 |

*Primary Examiner*—Walter D. Griffin
*Assistant Examiner*—Tam M. Nguyen
*Attorney, Agent, or Firm*—Jeffrey R. Anderson

[57] ABSTRACT

A process and/or system is provided for isomerizing a hydrocarbon feedstock comprising saturated $C_6$ hydrocarbons by contacting the hydrocarbon feedstock, in the presence of hydrogen and optionally a chloride, with a first isomerization catalyst composition in a first isomerization reactor defining a first reaction zone operated at a first reaction temperature, withdrawing a first intermediate stream comprising cyclohexane and n-hexane from the first reaction zone, separating the first intermediate stream, via a first separator, into a first product stream comprising cyclohexane and a second intermediate stream comprising n-hexane, contacting the second intermediate stream, in the presence of hydrogen and optionally a chloride, with a second isomerization catalyst composition in a second isomerization reactor defining a second reaction zone operated at a second reaction temperature greater than the first reaction temperature, and withdrawing from the second reaction zone a second product stream comprising isohexane.

17 Claims, 1 Drawing Sheet

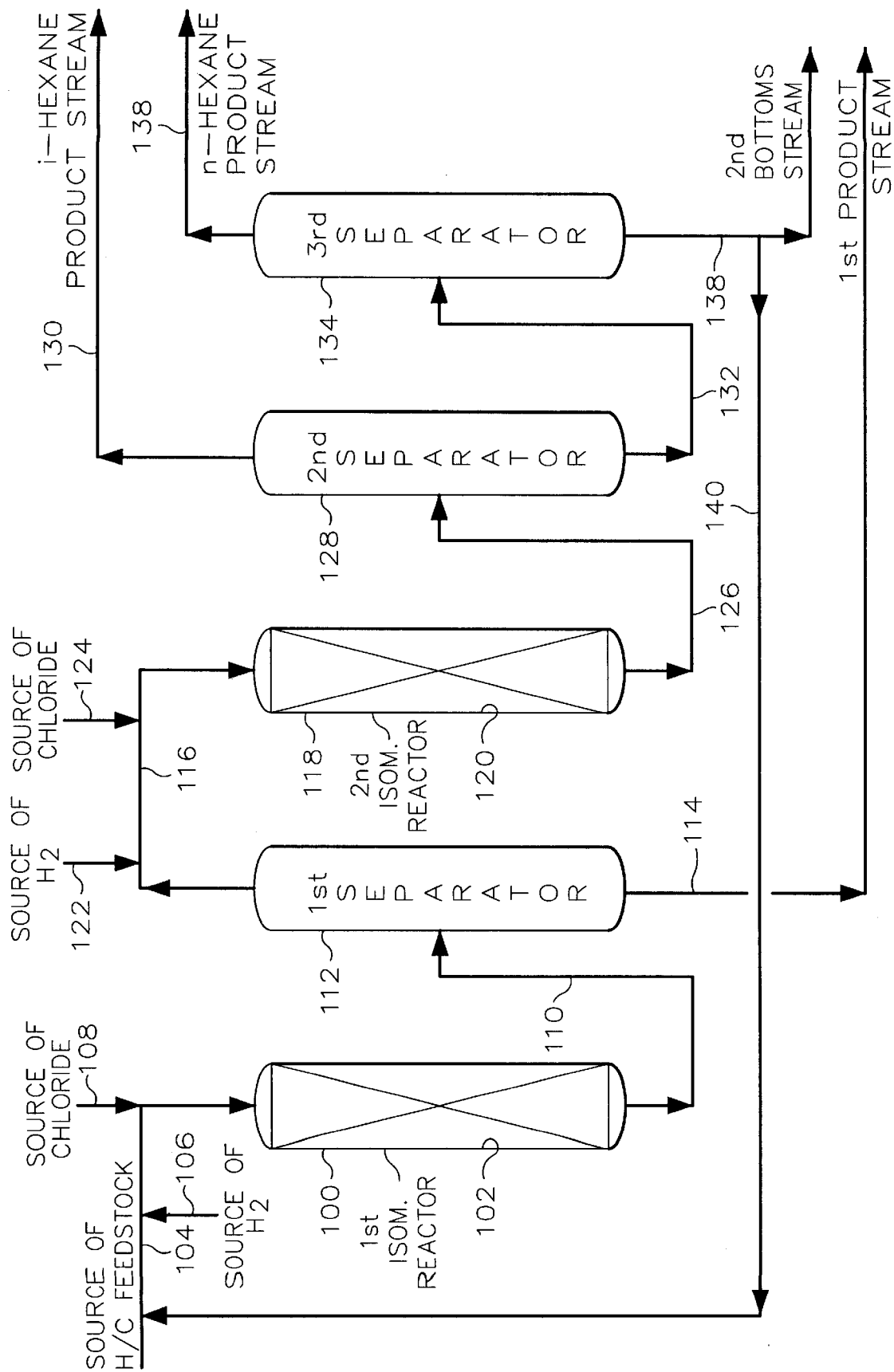

TWO-STAGE ISOMERIZATION OF SATURATED C6 HYDROCARBONS

This invention relates to an improved process for the isomerization of saturated $C_6$ hydrocarbons. More particularly, this invention relates to a two stage process for the isomerization of saturated $C_6$ hydrocarbons.

In the isomerization of saturated $C_6$ hydrocarbons there are two primary reactions of importance.

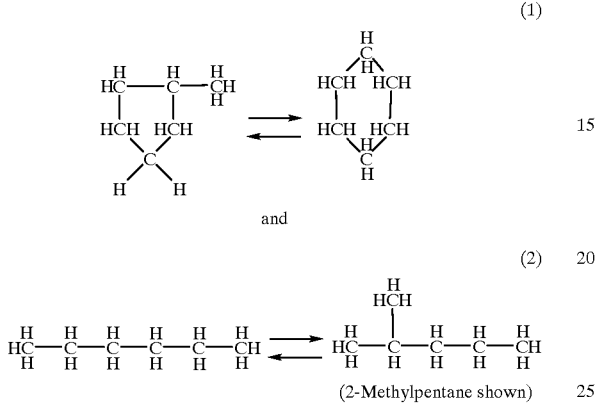

(2-Methylpentane shown)

Catalysts and processes for isomerizing saturated $C_6$ hydrocarbons are well known by those skilled in the art, and are described in the patent literature, e.g. in U.S. Pat. Nos. 3,054,832, 3,233,001, 3,277,194, 3,974,061, 4,655,484, 4,149,993, and 5,336,692. However, there are ever present incentives for the development of new and/or more effective processes for isomerizing saturated $C_6$ hydrocarbons and for providing flexibility in the process to allow preferential production of one $C_6$ product over another $C_6$ product.

SUMMARY OF THE INVENTION

It is an object of this invention to provide a novel process and/or system for isomerizing saturated $C_6$ hydrocarbons.

A further object of this invention is to provide an improved isomerization process and/or system of increased efficiency.

It is yet a further object of this invention to provide a two stage isomerization process and/or system useful for isomerizing methylcyclopentane to cyclohexane and for isomerizing n-hexane to isohexanes.

In accordance with the present invention, a process for isomerizing a hydrocarbon feedstock comprising saturated $C_6$ hydrocarbons is provided including the following steps:
contacting the hydrocarbon feedstock, in the presence of hydrogen, with a first isomerization catalyst composition in a first reaction zone operated under reaction conditions for isomerizing hydrocarbons including a first reaction temperature;
withdrawing from the first reaction zone a first intermediate stream comprising cyclohexane and n-hexane;
separating the first intermediate stream into a first product stream comprising cyclohexane and a second intermediate stream comprising n-hexane;
contacting the second intermediate stream, in the presence of hydrogen, with a second isomerization catalyst composition in a second reaction zone operated under reaction conditions for isomerizing hydrocarbons including a second reaction temperature greater than the first reaction temperature of the first reaction zone; and
withdrawing from the second reaction zone a second product stream comprising isohexane.

The process can further include the steps of:
separating the second product stream into an isohexane product stream comprising isohexane and a first bottoms stream comprising n-hexane, methylcyclopentane and cyclohexane;
separating the first bottoms stream into a n-hexane product stream comprising n-hexane and a second bottoms stream comprising methylcylcopentane and cyclohexane; and
introducing at least a portion of the second bottoms stream into the first reaction zone.

In accordance with another embodiment of the present invention, a system for isomerizing a hydrocarbon feedstock comprising saturated $C_6$ hydrocarbons is provided comprising:
a first isomerization reactor containing a first isomerization catalyst composition;
first conduit means operably related to the first isomerization reactor for introducing the hydrocarbon feedstock into the first isomerization reactor;
second conduit means operably related to the first conduit means for introducing a hydrogen stream into the first isomerization reactor;
third conduit means operably related to the first conduit means for introducing a chloride into the first isomerization reactor;
fourth conduit means operably related to the first isomerization reactor and operably related to a first separator for withdrawing a first intermediate stream comprising cyclohexane and n-hexane from the first isomerization reactor and for introducing the first intermediate stream into the first separator, the first separator providing means for separating the first intermediate stream into a first product stream comprising cyclohexane and a second intermediate stream comprising n-hexane;
fifth conduit means operably related to the first separator for withdrawing the first product stream from the first separator;
sixth conduit means operably related to the first separator and operably related to a second isomerization reactor for withdrawing the second intermediate stream from the first separator and for introducing the second intermediate stream into the second isomerization reactor, the second isomerization reactor containing a second isomerization catalyst composition;
seventh conduit means operably related to the sixth conduit means for introducing a hydrogen stream into the second isomerization reactor;
eighth conduit means operably related to the sixth conduit means for introducing a chloride into the second isomerization reactor; and
ninth conduit means operably related to the second isomerization reactor for withdrawing a second product stream comprising isohexane from the second isomerization reactor.

The ninth conduit means can also be operably related to a second separator for introducing the second product stream into the second separator, the second separator providing means for separating the second product stream into an isohexane product stream comprising isohexane and a first bottoms stream comprising n-hexane, methylcyclopentane and cyclohexane; and the system can further include:
tenth conduit means operably related to the second separator for withdrawing the isohexane product stream from the second separator;

eleventh conduit means operably related to the second separator and operably related to a third separator for withdrawing the first bottoms stream from the second separator and for introducing the first bottoms stream into the third separator, the third separator providing means for separating the first bottoms stream into a n-hexane product stream comprising n-hexane and a second bottoms stream comprising methylcyclopentane and cyclohexane;

twelfth conduit means operably related to the third separator for withdrawing the n-hexane product stream from the third separator;

thirteenth conduit means operably related to the third separator for withdrawing the second bottoms stream from the third separator; and fourteenth conduit means operably related to the thirteenth conduit means and operably related to the first isomerization reactor for recycling at least a portion of the second bottoms stream to the first isomerization reactor.

Other objects and advantages will become apparent from the detailed description and the appended claims.

BRIEF DESCRIPTION OF THE DRAWING

The FIGURE is a schematic flow diagram presenting an embodiment of the present invention.

DETAILED DESCRIPTION OF THE INVENTION

An important aspect of the inventive isomerization process is the use of saturated $C_6$ hydrocarbons as a hydrocarbon feedstock.

The hydrocarbon feedstock can comprise saturated $C_6$ hydrocarbons including, but not limited to, methylcyclopentane and n-hexane.

The hydrocarbon feedstock can comprise n-hexane in the range from about 1 to about 99 weight %, more particularly from about 10 to about 90 weight %, and most particularly from 20 to 60 weight %, based on the total weight of the hydrocarbon feedstock. The hydrocarbon feedstock can further comprise methylcyclopentane in the range of from about 1 to about 60 weight %, more particularly from about 10 to about 50 weight %, and most particularly from 15 to 40 weight %, based on the total weight of the hydrocarbon feedstock.

The hydrocarbon feedstock can be isomerized by contact with a first isomerization catalyst composition, in any suitable manner, within a first reaction zone to produce a first intermediate stream comprising methylcyclopentane, cyclohexane, n-hexane and isohexane.

The isohexane can be in the form of 2-methylpentane, 3-methylpentane, 2,3-dimethylbutane, and 2,2-dimethylbutane. The preferred isohexane is 2,2-dimethylbutane.

The isomerization of the hydrocarbon feedstock within the first reaction zone is preferably carried out in the presence of hydrogen and under reaction conditions such that the first intermediate stream has an increased concentration of cyclohexane as compared to the cyclohexane concentration of the hydrocarbon feedstock.

Preferably, the reaction conditions of the first reaction zone are such that the methylcyclopentane conversion to cyclohexane is greater than about 25 weight %, more preferably greater than about 30 weight %, and most preferably greater than 40 weight %, based on the total weight of the methylcyclopentane introduced to the first reaction zone.

The reaction conditions of the first reaction zone more particularly include a first reaction temperature in the range of from about 110° F. to about 210° F.; preferably from about 120° F. to about 200° F.; and most preferably from 130° F. to 190° F. Generally the reaction conditions of the first reaction zone further include a reaction pressure in the range of from about 150 psig to about 1500 psig, preferably from about 200 psig to about 1200 psig; and most preferably from 250 psig to 1000 psig; and a liquid hourly space velocity (LHSV) of the hydrocarbon feedstock, defined as cubic centimeters (cc) of liquid feed hydrocarbon per cc of catalyst per hour, in the range of from about 0.01 hr.$^{-1}$ to about 1000 hr.$^{-1}$, preferably from about 0.25 hr.$^{-1}$ to about 250 hr.$^{-1}$, and most preferably from 0.5 hr.$^{-1}$ to 10 hr.$^{-1}$.

The hydrogen-to-saturated hydrocarbon molar ratio in the first reaction zone is preferably at least about 0.01:1, more preferably in the range of from about 0.01:1 to about 5:1, and most preferably from 0.02:1 to 2:1. The hydrocarbon feedstock and hydrogen can be contacted with the inventive catalyst system by any suitable manner. The contacting step can be operated as a batch process step or, preferably, as a continuous process step. In the latter operation, a solid catalyst bed or a moving catalyst bed or a fluidized catalyst bed can be employed. The contacting step can also be operated in downflow or upflow mode. Any of these operational modes have advantages and disadvantages, and those skilled in the art can select the one most suitable for a particular feed and catalyst.

The first isomerization catalyst composition useful in the first isomerization reaction zone can be any catalyst composition capable of converting methylcyclopentane to cyclohexane under the reaction conditions described above.

Preferably, the first isomerization catalyst composition comprises at least one Group VIII metal, a porous carrier material, and at least one halogen.

The Group VIII metal includes, but is not limited to, iron, cobalt, nickel, ruthenium, rhodium, palladium, osmium, iridium, and platinum. The preferred Group VIII metal is platinum.

The porous carrier material is preferably adsorptive with a high surface area in the range of from about 25 to about 500 m$^2$/g. Examples of suitable porous carrier materials include, but are not limited to, aluminas such as for example α-alumina and γ-alumina, silicas, alumina-silica; aluminum phosphate, aluminum chlorohydrate; clays such as kaolinite, halloysite, vermiculite, chlorite, attapulgite, smectite, montmorillonite, illite, saconite, sepiolite, palygorskite; activated carbon; coke; charcoal; crystalline zeolitic aluminosilicates (such as ZSM-5); and spinels such as $MgAl_2O_4$, $FeAl_2O_4$, $ZnAl_2O_4$ and $CaAl_2O_4$ and combinations of any two or more thereof. Because these porous carrier materials are well known to one skilled in the art, description of which is omitted herein. The presently preferred porous carrier material is alumina because it is readily available.

The halogen can be fluorine, chlorine, bromine, iodine, astatine, and mixtures of any two or more thereof. The presently preferred halogen is chlorine.

In order to activate the catalyst system and to retard its deactivation during the isomerization reaction, a chloride is frequently added to the hydrocarbon feedstock in an amount such that the chloride is present in the hydrocarbon feedstock in the range of from about 0.001 weight % to about 1 weight % based on the total weight of the hydrocarbon feedstock. The chloride is generally in the form of at least one chloroalkane, such as, but not limited to, carbon tetrachloride, chloroform, ethylchloride, isopropylchloride, tetrachloroethylene (also known as perchloroethylene, or PCE) and trichloroethane, tetrachloroethylene is preferred.

The first intermediate stream can be separated into a first product stream comprising cyclohexane, methylcyclopentane and n-hexane, and a second intermediate stream comprising n-hexane, isohexane, methylcyclopentane and cyclohexane.

The concentration of cyclohexane in the first product stream is preferably greater than about 50 weight %, more preferably greater than about 60 weight %, and most preferably greater than 70 weight %, based on the total weight of the first product stream.

The first product stream can be further processed downstream, such as by separation techniques, to produce a substantially pure cyclohexane product stream.

The second intermediate stream preferably comprises n-hexane at a concentration greater than about 30 weight %, more preferably greater than about 40 weight %, and most preferably greater than 50 weight %, and further comprises isohexane at a concentration greater than about 30 weight %, more preferably greater than about 40 weight %, and most preferably greater than 45 weight %, based on the total weight of the second intermediate stream.

The second intermediate stream can be isomerized by contact with a second isomerization catalyst composition, in any suitable manner, within a second reaction zone to produce a second product stream comprising isohexane, n-hexane, methylcyclopentane and cyclohexane.

The isomerization of the second intermediate stream within the second reaction zone is preferably carried out in the presence of hydrogen and under reaction conditions such that the second product stream has an increased concentration of isohexane as compared to the isohexane concentration of the second intermediate stream.

Preferably, the reaction conditions of the second reaction zone are such that the conversion of n-hexane to isohexane is greater than about 10 weight %, more preferably greater than about 15 weight %, and most preferably greater than 20 weight %, based on the total weight of n-hexane introduced to the second reaction zone.

The reaction conditions of the second reaction zone more particularly include a second reaction temperature greater than the first reaction temperature of the first reaction zone. The increased temperature for the second reaction zone (second reaction temperature) above that for the first reaction zone (first reaction temperature) allows preferential production of isohexane from the isomerization of n-hexane as compared to the lower first reaction zone temperature which allows preferential production of cyclohexane from the conversion of methylcyclopentane.

The second reaction temperature is preferably in the range of from about 200° F. to about 350° F., more preferably from about 220° F. to about 320° F., and most preferably from 240° F. to 300° F. The reaction conditions of the second reaction zone further include a reaction pressure in the range of from about 150 psig to about 1500 psig, preferably from about 200 psig to about 1200 psig, and more preferably from 250 psig to 1000 psig; and a LHSV in the range of from about 0.01 hr.$^{-1}$ to about 1000 hr.$^{-1}$, preferably from about 0.25 hr.$^{-1}$ to about 250 hr.$^{-1}$, and most preferably from 0.5 hr.$^{-1}$ to about 10 hr.$^{-1}$.

The hydrogen-to-saturated hydrocarbon molar ratio in the second reaction zone is preferably at least about 0.01:1, more preferably in the range of from about 0.01:1 to about 5:1, and most preferably from 0.02:1 to 2:1. The hydrocarbon feedstock and hydrogen can be contacted with the inventive catalyst system by any suitable manner. The contacting step can be operated as a batch process step or, preferably, as a continuous process step. In the latter operation, a solid catalyst bed or a moving catalyst bed or a fluidized catalyst bed can be employed. The contacting step can also be operated in downflow or upflow mode. Any of these operational modes have advantages and disadvantages, and those skilled in the art can select the one most suitable for a particular feed and catalyst.

The second isomerization catalyst composition useful in the second isomerization reaction zone can be any catalyst composition capable of converting n-hexane to isohexane under the reaction conditions described above.

Preferably, the second isomerization catalyst composition comprises at least one Group VIII metal, a porous carrier material, and at least one halogen, all as described above for the first isomerization catalyst composition.

The low first reaction temperature of the first reaction zone shifts the equilibrium of the methylcylcopentane-to-cyclohexane reaction preferentially toward cyclohexane. The higher second reaction temperature of the second reaction zone shifts the equilibrium of the n-hexane-to-isohexane reaction preferentially toward isohexane. The removal of cyclohexane from the first reaction zone effluent prior to introduction of the remainder to the second reaction zone provides the benefit of avoiding the conversion of cyclohexane back to methylcyclopentane at the higher second reaction temperature. Thus, the inventive process maximizes the conversions of methylcyclopentane and n-hexane to cyclohexane and isohexane, respectively, by taking advantage of the temperature sensitivities of the conversion reactions.

In another further embodiment, the second product stream can be separated into an isohexane product stream comprising isohexane, n-hexane, methylcyclopentane and cyclohexane; and a first bottoms stream comprising n-hexane, methylcyclopentane and cyclohexane.

The isohexane product stream preferably comprises isohexane at a concentration greater than about 50 weight %, more preferably greater than about 55 weight %, and most preferably greater than 60 weight %, based on the total weight of the isohexane product stream. The isohexane product stream can be passed downstream to become a part of a motor fuel blend.

The first bottoms stream can be separated into a n-hexane product stream comprising n-hexane, methylcyclopentane and cyclohexane; and a second bottoms stream comprising methylcyclopentane and cyclohexane.

The n-hexane product stream preferably comprises n-hexane at a concentration greater than about 70 weight %, more preferably greater than about 80 weight %, and most preferably greater than 90 weight %, based on the total weight of the n-hexane product stream.

The second bottoms stream typically comprises methylcyclopentane at a concentration greater than about 25 weight %, more typically greater than about 30 weight %, and most typically greater than 40 weight %, based on the total weight of the second bottoms stream. At least a portion of the second bottoms stream can be introduced into the first reaction zone for contact with the first isomerization catalyst composition to thereby convert at least a portion of the methylcyclopentane contained in the second bottoms stream to cyclohexane.

Those skilled in the art can vary the composition of the hydrocarbon feedstock, the first reaction temperature, the second reaction temperature, or the severity of the separation steps in order to optimize the production of the desired products, such as, cyclohexane, isohexane, or n-hexane.

Referring to the FIGURE, therein is illustrated the system 10 which is suitable for performing the inventive process. The system 10 includes a first isomerization reactor 100 having an inside wall 102 which defines a first reaction zone containing a first isomerization catalyst composition. The first isomerization reactor 100 is connected in fluid flow communication with a conduit 104 providing first conduit means for introducing a hydrocarbon feedstock comprising methylcyclopentane and n-hexane into the first isomerization reactor 100. Conduit 104 is connected in fluid flow communication with a conduit 106 providing second conduit means for introducing a hydrogen stream into first isomerization reactor 100. Conduit 104 is also connected in fluid flow communication with a conduit 108 providing third conduit means for introducing a chloride into first isomerization reactor 100. The first reaction zone provides means for isomerizing the hydrocarbon feedstock to thereby produce a first intermediate stream comprising cyclohexane and n-hexane.

First isomerization reactor 100 is connected in fluid flow communication via conduit 110 to a first separator 112 and conduit 110 provides fourth conduit means for withdrawing the first intermediate stream from the first isomerization reactor 100 and for introducing the first intermediate stream into the first separator 112. First separator 112 provides means for separating the first intermediate stream into a first product stream comprising cyclohexane and a second intermediate stream comprising n-hexane. First separator 112 is connected in fluid flow communication with conduit 114 providing fifth conduit means for withdrawing the first product stream from first separator 112 for further downstream processing. First separator 112 is also connected in fluid flow communication via conduit 116 to a second isomerization reactor 118 and conduit 116 provides sixth conduit means for withdrawing the second intermediate stream from the first separator 112 and for introducing the second intermediate stream into the second isomerization reactor 118 having an inside wall 120 which defines a second reaction zone containing a second isomerization catalyst composition. Conduit 116 is connected in fluid flow communication with a conduit 122 providing seventh conduit means for introducing a hydrogen stream into second isomerization reactor 118. Conduit 116 is also connected in fluid flow communication with a conduit 124 providing eighth conduit means for introducing a chloride into second isomerization reactor 118. The second reaction zone provides means for isomerizing the second intermediate stream to thereby produce a second product stream comprising isohexane. The second isomerization reactor 118 is connected in fluid flow communication with conduit 126 providing ninth conduit means for withdrawing the second product stream from the second isomerization reactor 118.

Conduit 126 is optionally connected in fluid flow communication with a second separator 128 and provides ninth conduit means for introducing the second product stream into the second separator 128. Second separator 128 provides means for separating the second product stream into an isohexane product stream comprising isohexane and a first bottoms stream comprising n-hexane, methylcyclopentane and cyclohexane. Second separator 128 is connected in fluid flow communication with conduit 130 providing tenth conduit means for withdrawing the isohexane product stream for further downstream processing. Second separator 128 is also connected in fluid flow communication via conduit 132 to a third separator 134 and conduit 132 provides eleventh conduit means for withdrawing the first bottoms stream from the second separator 128 and for introducing the first bottoms stream into the third separator 134. Third separator 134 provides means for separating the first bottoms stream into a n-hexane product stream comprising n-hexane and a second bottoms stream comprising methylcyclopentane and cyclohexane. Third separator 134 is connected in fluid flow communication with conduit 136 providing twelfth conduit means for withdrawing the n-hexane product stream for further downstream processing. Third separator 134 is also connected in fluid flow communication with conduit 138 providing thirteenth conduit means for withdrawing the second bottoms stream from the third separator 134. Conduit 138 is connected in fluid flow communication with conduit 140 providing fourteenth conduit means for recycling at least a portion of the second bottoms stream to first isomerization reactor 100. The remainder of the second bottoms stream passes downstream in conduit 138 for further downstream processing.

The following example is provided to further illustrate this invention and is not to be considered as unduly limiting the scope of this invention.

EXAMPLE

This example illustrates the benefit of increased methylcyclopentane and n-hexane isomerization to cyclohexane and isohexane, respectively, using the inventive process.

Run 1 (Control)

First and second stainless-steel reactors (each having an inner diameter of about 0.75 inch and a height of about 28 inches) were each filled with a layer (about 13.5 inches high) of inert alumina particles having a surface area of 1 $m^2$/g or less, a layer (about 6 inches high) of 1–8 Pt/alumina isomerization catalyst (marketed by UOP, Des Plaines, Ill.; containing about 0.2 weight-% Pt, about 45 weight-% Al, about 2.9 weight-% Cl, about 0.07 weight-% Mg, about 0.07 weight-% Ti, and the remainder being essentially chemically bound oxygen and hydrogen; surface area: 195 $m^2$/g) and a top layer (about 8 inches high) of the inert alumina described above.

A stream of hydrogen gas was combined with a liquid hydrocarbon feed comprising alkanes from a commercial refinery to form a first mixture which was heated to about 260° F. PCE was injected into the first mixture at a rate of 0.89 microliters/hour prior to the introduction of the first mixture into the first reactor at a liquid hourly space velocity of about 2 $hour^{-1}$. The reaction pressure in the first reactor was in the range of from about 300 psig to about 450 psig. The hydrogen-to-hydrocarbon ($H_2$:HC) molar ratio of the first mixture was about 0.06:1. A portion of the first reactor product was analyzed by means of a gas chromatograph. Test data for the first reactor product obtained after 7 hours on stream are summarized in Table 1.

A stream of hydrogen gas was combined with the remainder of the first reactor product to form a second mixture which was cooled to about 170° F. PCE was injected into the second mixture at a rate of 0.89 microliters/hour prior to the introduction of the second mixture into the second reactor at a liquid hourly space velocity of about 2 $hour^{-1}$. The reaction pressure in the second reactor was in the range of from about 300 psig to about 450 psig. The $H_2$:HC molar ratio of the second mixture was about 0.06:1. The second reactor product was analyzed by means of a gas chromatograph. Test data for the second reactor product obtained after 7 hours on stream are summarized in Table 1.

TABLE 1

(control)

| Component | Hydrocarbon Feed, wt. % | First reactor product (at 260 °F.), wt. % | Second reactor product (at 170 °F.), wt. % |
|---|---|---|---|
| methylcyclopentane | 28.3 | 18.2 | 12.4 |
| n-hexane | 51.5 | 20.8 | 18.7 |
| cyclohexane | 12.6 | 22.7 | 28.4 |
| 2,2 DMB | 0 | 5.0 | 5.8 |
| 2,3 DMB + 2MP + 3MP | 7.1 | 32.9 | 34.1 |
| Total isohexane | 7.1 | 37.9 | 39.9 |
| $C_7+$ | 0.5 | 0.4 | 0.6 |
| Total | 100 | 100 | 100 |

2,2 DMB = 2,2 Dimethylbutane
2,3 DMB = 2,3 Dimethylbutane
2MP = 2-Methylpentane
3MP = 3-Methylpentane Run 2 (Invention)

First and second stainless-steel reactors (each having an inner diameter of about 0.75 inch and a height of about 28 inches) were each filled with a layer (about 13.5 inches high) of inert alumina particles having a surface area of 1 $m^2/g$ or less, a layer (about 6 inches high) of 1–8 Pt/alumina isomerization catalyst (marketed by UOP, Des Plaines, Ill.; containing about 0.2 weight-% Pt, about 45 weight-% Al, about 2.9 weight-% Cl, about 0.07 weight-% Mg, about 0.07 weight-% Ti, and the remainder being essentially chemically bound oxygen and hydrogen; surface area: 195 $m^2/g$) and a top layer (about 8 inches high) of the inert alumina described above.

A stream of hydrogen gas was combined with a liquid hydrocarbon feed comprising alkanes from a commercial refinery to form a first mixture which was heated to about 170° F. PCE was injected into the first mixture at a rate of 0.89 microliters/hour prior to the introduction of the first mixture into the first reactor at a liquid hourly space velocity of about 2 $hour^{-1}$. The reaction pressure in the first reactor was in the range of from about 300 psig to about 450 psig. The $H_2$:HC molar ratio of the first mixture was about 0.06:1. A portion of the first reactor product was analyzed by means of a gas chromatograph. Test data for the first reactor product obtained after 7 hours on stream are summarized in Table 2.

The remainder of the first reactor product was separated via distillation into a cyclohexane (Cy $C_6$) product stream and a second reactor feed. Portions of the cyclohexane product stream and second reactor feed were analyzed by means of a gas chromatograph. Test data for the cyclohexane product stream and second reactor feed obtained after 7 hours on stream are summarized in Table 2.

A stream of hydrogen gas was combined with the remainder of the second reactor feed to form a second mixture which was heated to about 260° F. PCE was injected into the second mixture at a rate of 0.89 microliters/hour prior to the introduction of the second mixture into the second reactor at a liquid hourly space velocity of about 2 $hour^{-1}$. The reaction pressure in the second reactor was in the range of from about 300 psig to about 450 psig. The $H_2$:HC molar ratio of the second mixture was about 0.06:1. The second reactor product was analyzed by means of a gas chromatograph. Test data for the second reactor product obtained after 7 hours on stream are summarized in Table 2.

Table 3 summarizes overall n-$C_6$ conversion, overall MCP conversion and 2,2 DMB selectivity for Runs 1 and 2.

TABLE 2

(invention)

| Component | Hydrocarbon Feed, wt. % | First reactor product (at 170 °F.), wt. % * | CyC6 product stream wt. % * | Second reactor feed, wt. % * | Second reactor product (at 260 °F.), wt. % * | Overall product wt. % * |
|---|---|---|---|---|---|---|
| methylcyclopentane | 28.3 | 12.4 | 0.2 | 12.2 | 7.3 | 7.5 |
| n-hexane | 51.5 | 37.4 | 0.9 | 36.5 | 16.9 | 17.8 |
| cyclohexane | 12.6 | 28.4 | 24.1 | 4.3 | 9.2 | 33.3 |
| 2,2 DMB | 0 | 1.4 | 0 | 1.4 | 6.2 | 6.2 |
| 2,3 DMB + 2MP + 3MP | 7.1 | 19.8 | 0.6 | 19.2 | 34.0 | 34.6 |
| Total isohexane | 7.1 | 21.2 | 0.6 | 20.6 | 40.2 | 40.8 |
| $C_7+$ | 0.5 | 0.6 | 0.6 | — | — | 0.6 |
| Total | 100 | 100 | 26.4 | 73.6 | 73.6 | 100 |

\* - wt. % based on the total weight of the hydrocarbon feed
2,2 DMB = 2,2 Dimethylbutane
2,3 DMB = 2,3 Dimethylbutane
2MP = 2-Methylpentane
3MP = 3-Methylpentane

TABLE 3

| | Overall n-$C_6$ conv.[1], wt. % | Overall MCP conv.[2], wt. % | 2,2-DMB select.[3], % |
|---|---|---|---|
| Run 1 | 63.7 | 56.2 | 14.5 |
| Run 2 | 65.4 | 73.5 | 15.4 |

[1]n-$C_6$ conversion is the % conversion of n-hexane in the hydrocarbon feed to isohexane.
[2]MCP conversion is the % conversion of methylcyclopentane in the hydrocarbon feed to cyclohexane.
[3]2,2-DMB selectivity is the molar ratio of 2,2-Dimethylbutane in the second reactor product to all isohexanes in the second reactor product, multiplied by 100.

The test data presented in the Tables show that use of the inventive process in Run 2 produced considerably higher conversions of n-hexane and methylcylcopentane than the control process in Run 1.

Inventive Run 2 demonstrated 2.7% and 30.8% increases in conversion of n-hexane and methylcyclopentane, respectively, over control Run 1.

Inventive Run 2 also demonstrated a 6.2% increase in 2,2-dimethylbutane selectivity in the second reactor product over control Run 1.

From the test data presented in the Tables it is readily apparent that the invention (Run 2) provides an improved process and/or system for isomerizing MCP to cyclohexane and for isomerizing n-$C_6$ to iso-hexanes as compared to the process and/or system of control Run 1.

Reasonable variations, modifications, and adaptations can be made within the scope of the disclosure and the appended claims without departing from the scope of this invention.

That which is claimed is:

1. A process for isomerizing a hydrocarbon feedstock comprising saturated $C_6$ hydrocarbons, said process comprising the steps of:
    contacting said hydrocarbon feedstock, in the presence of hydrogen, with a first isomerization catalyst composition in a first reaction zone operated under reaction conditions for isomerizing hydrocarbons including a first reaction temperature;
    withdrawing from said first reaction zone a first intermediate stream comprising cyclohexane and n-hexane;
    separating said first intermediate stream into a first product stream comprising cyclohexane and a second intermediate stream comprising n-hexane;
    contacting said second intermediate stream, in the presence of hydrogen, with a second isomerization catalyst composition in a second reaction zone operated under reaction conditions for isomerizing hydrocarbons including a second reaction temperature greater than said first reaction temperature of said first reaction zone; and
    withdrawing from said second reaction zone a second product stream comprising isohexane.

2. A process as recited in claim 1 wherein said hydrocarbon feedstock is contacted with said first isomerization catalyst composition in the presence of hydrogen and a chloride; and wherein said second intermediate stream is contacted with said second isomerization catalyst composition in the presence of hydrogen and a chloride.

3. A process as recited in claim 1 wherein said first reaction temperature is in the range of from about 110° F. to about 210° F., and wherein said second reaction temperature is in the range of from about 200° F. to about 350° F.

4. A process as recited in claim 3 wherein said reaction conditions of said first reaction zone and said reaction conditions of said second reaction zone include a hydrogen-to-hydrocarbon molar ratio at least about 0.01:1, a pressure in the range of from about 150 psig to about 1500 psig, and a LHSV in the range of from about 0.01 hr.$^{-1}$ to about 1000 hr.$^{-1}$.

5. A process as recited in claim 1 wherein said saturated $C_6$ hydrocarbons comprise n-hexane and methylcyclopentane.

6. A process as recited in claim 1 wherein said hydrocarbon feedstock contains n-hexane in the range of from about 1 to about 99 weight % based on the total weight of said hydrocarbon feedstock; and wherein said hydrocarbon feedstock contains methylcyclopentane in the range of from about 1 to about 60 weight % based on the total weight of said hydrocarbon feedstock.

7. A process as recited in claim 1 wherein said first isomerization catalyst composition comprises at least one Group VIII metal, a porous carrier material, and at least one halogen.

8. A process as recited in claim 7 wherein said at least one Group VIII metal is platinum.

9. A process as recited in claim 7 wherein said porous carrier material is alumina.

10. A process as recited in claim 7 wherein said at least one halogen is chlorine.

11. A process as recited in claim 1 wherein said second isomerization catalyst composition comprises at least one Group VIII metal, a porous carrier material, and at least one halogen.

12. A process as recited in claim 11 wherein said at least one Group VIII metal is platinum.

13. A process as recited in claim 11 wherein said porous carrier material is alumina.

14. A process as recited in claim 11 wherein said at least one halogen is chlorine.

15. A process as recited in claim 11 further comprising the steps of:
    separating said second product stream into an isohexane product stream comprising isohexane and a first bottoms stream comprising n-hexane, methylcyclopentane and cyclohexane;
    separating said first bottoms stream into a n-hexane product stream comprising n-hexane and a second bottoms stream comprising methylcyclopentane and cyclohexane; and
    introducing at least a portion of said second bottoms stream into said first reaction zone.

16. A process for isomerizing a hydrocarbon feedstock comprising the steps of:
    contacting said hydrocarbon feedstock comprising n-hexane in the range of from about 1 to about 99 weight % and comprising methylcyclopentane in the range of from about 1 to about 60 weight % of said hydrocarbon feedstock, in the presence of hydrogen and a chloride, with a first isomerization catalyst composition comprising platinum, alumina and chlorine in a first reaction zone operated under reaction conditions for isomerizing hydrocarbons including a first reaction temperature in the range of from about 110° F. to about 200° F.;
    withdrawing from said first reaction zone a first intermediate stream comprising cyclohexane and n-hexane;
    separating said first intermediate stream into a first product stream comprising cyclohexane and a second intermediate stream comprising n-hexane;
    contacting said second intermediate stream, in the presence of hydrogen and a chloride, with a second isomerization catalyst composition comprising platinum, alumina and chlorine in a second reaction zone operated under reaction conditions for isomerizing hydrocarbons including a second reaction temperature in the range of from about 240° F. to about 300° F.; and
    withdrawing from said second reaction zone a second product stream comprising isohexane.

17. A process as recited in claim 16 further comprising the steps of:
    separating said second product stream into an isohexane product stream comprising isohexane and a first bottoms stream comprising n-hexane, methylcyclopentane and cyclohexane;
    separating said first bottoms stream into a n-hexane product stream comprising n-hexane and a second bottoms stream comprising methylcyclopentane and cyclohexane; and
    introducing at least a portion of said second bottoms stream into said first reaction zone.

* * * * *

UNITED STATES PATENT AND TRADEMARK OFFICE
CERTIFICATE OF CORRECTION

PATENT NO. : 6,133,496
DATED : October 17, 2000
INVENTOR(S) : Fan-nan Lin and Edgar Durand Davis It is certified that error appears in the above-identified patent and that said Letters Patent is hereby corrected as shown below:

Claim 15, Column 12:
Line 16 please delete "claim 11" and insert therefor ---claim 1---.

Signed and Sealed this

Twelfth Day of June, 2001

*Attest:*

*Attesting Officer*

NICHOLAS P. GODICI
*Acting Director of the United States Patent and Trademark Office*